(12) United States Patent
Pechstein et al.

(10) Patent No.: US 7,511,504 B2
(45) Date of Patent: Mar. 31, 2009

(54) METHOD AND DEVICE FOR MONITORING A REFERENCE HALF CELL

(75) Inventors: Torsten Pechstein, Radebeul (DE); Katrin Scholz, Bobritzsch (DE); Sven Häertig, Frankenhain (DE)

(73) Assignee: Endress + Hauser Conducta Gesellschaft fur Mess- u. Regeltechnik mbH + Co. KG, Gerlingen (DE)

( * ) Notice: Subject to any disclaimer, the term of this patent is extended or adjusted under 35 U.S.C. 154(b) by 301 days.

(21) Appl. No.: 10/534,972

(22) PCT Filed: Nov. 13, 2003

(86) PCT No.: PCT/EP03/12668

§ 371 (c)(1),
(2), (4) Date: Dec. 20, 2005

(87) PCT Pub. No.: WO2004/046708

PCT Pub. Date: Jun. 3, 2004

(65) Prior Publication Data

US 2006/0125481 A1 Jun. 15, 2006

(30) Foreign Application Priority Data

Nov. 15, 2002 (DE) ................................ 102 53 595

(51) Int. Cl.
*G01N 27/416* (2006.01)
*G01N 27/02* (2006.01)
*G01N 27/28* (2006.01)
*G01N 27/26* (2006.01)

(52) U.S. Cl. .................... 324/438; 324/439; 324/450; 204/401

(58) Field of Classification Search ................ 324/438, 324/439, 450; 204/401
See application file for complete search history.

(56) References Cited

U.S. PATENT DOCUMENTS

| 4,777,444 A * | 10/1988 | Beij et al. ................. 324/439 |
| 4,853,638 A * | 8/1989 | Endou et al. ................ 324/441 |
| 6,853,195 B2 * | 2/2005 | Gehrke et al. ............... 324/438 |

* cited by examiner

*Primary Examiner*—Timothy J Dole
(74) *Attorney, Agent, or Firm*—Bacon & Thomas, PLLC

(57) ABSTRACT

A method for monitoring a reference half cell, which forms with a measuring half cell a potentiometric measuring point for determining and/or monitoring an ion concentration of a medium. The ion concentration of the mediums determined on the basis of at least one measurement signal determined in a measuring circuit, between the measuring half cell and the reference half cell. According to the invention, the measuring point is operated intermittently in an operating mode and in a test mode, wherein, in the operating mode, the ion concentration is measured and wherein, in the test mode, the proper functioning of the reference half cell is checked.

11 Claims, 2 Drawing Sheets

METHOD AND DEVICE FOR MONITORING A REFERENCE HALF CELL

FIELD OF THE INVENTION

The invention relates to method and apparatus for monitoring a reference half cell, wherein the reference half cell forms with a measuring half cell a potentiometric measuring point for determining and/or monitoring an ion concentration of a medium and wherein the ion concentration of the medium is determined on the basis of a measured value determined in the measuring circuit between the measuring half cell and the reference half cell.

BACKGROUND OF THE INVENTION

In the case of the potentiometric measuring point for determining the ion concentration in a liquid medium, for instance, a pH sensor. The pH sensor can be embodied as a glass electrode or as an ISFET sensor. The voltage which forms between the measuring half cell and the reference half cell serves as a measure for the pH value, or for the ion concentration of the medium. The fundamentals of pH measurement technology and the construction of pH sensors are described, for example, in the book "Abwasser-Meβ-und Regeltechnik" (Wastewater-Measuring and Control Technology), Publisher: Endress+Hauser GmbH+Co., 2nd Ed., Pgs. 81 et seq.

Preferably, the pH-measuring half cells are so-called glass electrodes or ISFET sensors. These find broad application in many branches of chemistry, environmental testing, medicine, industry and water management. Both types of sensors are available from the assignee for the most varied of applications. As already indicated, the glass electrodes and ISFET sensors used for potentiometric measurements are commonly combined with reference half cells, which exhibit highly constant potentials.

In the case of glass electrodes, silver/silver-chloride or calomel electrodes are, as a rule, used. The contact of the reference half cell with the medium being measured is produced by way of bridge electrolytes. The bridge electrolyte can be liquid or solid and must, as a rule, fulfill certain prerequisites: On the one hand, it should have little influence on the potential of the reference half cell; on the other hand, it should form with the medium being measured a smallest possible diffusion potential. Provided that the prerequisites are fulfilled, the reference half cell provides a process-independent and stable reference signal.

In many instances of application of pH, REDOX and ISE measurement technology, liquid-bridged reference half cells are used. Liquid-bridged reference half cells use a liquid contact between the process—i.e. the medium—and the interior of the reference half cell. This liquid contact is usually provided in the form of a porous ceramic rod with a pore diameter in the μm-range. Now, process factors can lead to a plugging of this porous ceramic. If a plugging or blocking of the ceramic occurs, the junction assumes a very high resistance and no longer provides a low-resistance coupling of the reference half cell to the medium. Consequently, disturbance voltages can become superimposed on the potential of the reference half cell, and these can, among other things, significantly compromise the accuracy of measurement. In the case of a pH-value measurement, these disturbance voltages can even correspond to changes of multiple pH-values. As a result of the disturbance voltages, the measuring point then outputs pH-values no longer reflecting the actual ion concentration in the medium. In practice, moreover, about 90% of the bad measurements occurring in the case of ion concentration measurements are caused by a malfunctioning of the reference half cell.

A method does already exist for recognizing a malfunctioning of a reference half cell caused by the blocking of the junction between the reference half cell and the medium being measured. According to this known method, a malfunctioning of the reference half cell is recognized by monitoring in the process the impedance of the liquid junction between the reference half cell and the medium being measured. As soon as a predetermined limit value is exceeded, an alarm is activated.

FIG. 1 shows the essential components of a pH measuring point 1, as is used in measurement technology. The measurement point 1 includes a measuring half cell 2, a reference half cell 3 and a measuring device 6, which usually measures the voltage between the two half cells 2, 3. This voltage is inversely proportional to the pH-value of the medium 7 being measured.

The pH-measuring half cell 2 usually has an internal resistance of 50 to 1000 M. Via the medium 7 being measured, there is a connection to the liquid-bridged reference half cell. This connection usually has an impedance in the order of magnitude of 1-100 k and, therefore, lies at a few orders of magnitude below the impedance of the measuring half cell 2. The measuring device 6 determines the voltage between the two half cells 2, 3, with the reference half cell 3 lying at ground potential in the measuring device. Due to the relatively low impedance of the liquid-bridged reference half cell 3, the medium 7 is, consequently, also at the ground potential, up to the glass membrane. If a blockage of the liquid-bridged reference half cell 3 arises, then electrical disturbance potentials between the measuring half cell 2 and the reference half cell 3 become noticeable in the measuring. Since the measuring half cell 2 and the reference half cell 3 are, considered electrically, connected in series, the sum of the impedances is dominated by the impedance of the measuring half cell 2. For this reason, as illustrated in FIG. 1, a simple resistance measurement between the points I and II does not allow any conclusion as to the impedance of the reference half cell 3 at the moment.

In order to achieve a targeted monitoring of the impedance of the reference half cell 3, it is known to use a symmetrically-connected measuring point 1. A circuit of this type is displayed schematically in FIG. 2. The measuring half cell 2 is operated at low resistance relative to a metal rod 10; the reference half cell 3 is also measured relative to the metal rod 10. The metal rod 10 has the advantage, as compared to the reference half cell 3, that it does not get blocked. It is true that the metal rod 10 does not deliver a constant reference potential, since redox potentials can develop on it. This is, however, not of concern for the measurements by means of the measuring devices 8 and 9, since, in the end, the difference of the measured values from the two measurements is formed, so that the influence of the changing redox potentials on the metal rod 10 drops out. Consequently, the impedance measured between the two points I and II depends essentially on the impedance of the liquid-bridged reference half cell 2. Therefore, this method is ideally suited for recognizing a malfunctioning of the reference half cell 3 due to blocking.

The disadvantages of this known solution are, however, not to be overlooked:

A not insignificant extra burden has to be carried. Along with the extra metal rod, there is a more complicated suspension system, extra cable, and an expanded electronics.

An alarm indicating malfunctioning of the reference half cell is first triggered, after an earlier established limit value is exceeded. The alarm is activated completely independently of whether the increased value of the impedance of the reference half cell is, in fact, even affecting the measurement or whether the disturbance was perhaps already so grave, even before the reaching of the limit value, that the measurement was already at that time significantly affected.

SUMMARY OF THE INVENTION

An object of the invention is to provide a method and an apparatus permitting monitoring of the reference cell of a measuring point, with the monitoring being specially targeted at looking for a malfunctioning of the reference half cell.

The object is achieved as regards the method of the invention by operating the measuring point intermittently between an operating mode and a test mode, wherein, in the operating mode, the ion concentration is measured, and wherein, in the test mode, the proper functioning of the reference half cell is reviewed.

According to an advantageous further development of the method of the invention, it is provided that, in the test mode and in the operating mode, the noise portion of the measurement signal is determined. Additionally, it is provided that, in the test mode, for determining the noise portion of the measurement signal, an impedance, especially a resistance, is activated in the measuring circuit and that, in the operating mode, the impedance is changed. Preferably, in the operating mode, the resistance is short circuited.

An advantageous further development of the method of the invention provides that, for changing, i.e. for adding and removing, the impedance, especially the resistance, an impedance changing element is actuated. Especially, the impedance changing element is a switch, which is arranged e.g. in parallel with the resistance.

Moreover, it is provided that the noise portions of the measurement signal are measured in the operating mode and in the test mode, and that, on the basis of the relationship of the changes of the noise portions in the operating mode and in the test mode, a malfunctioning of the reference half cell is recognized and a corresponding report is issued.

A further development of the method of the invention enables a statement concerning the prospective remaining life of the reference half cell. To this end, the noise portions of the measurement signals, or the relationships of the changes of the noise portions of the measurement signals, in the operating mode and in the test mode, are continually stored; a report is issued as to when the reference half cell will probably malfunction.

The object is achieved as regards the apparatus of the invention in that the control/evaluation unit operates the measuring point intermittently in an operating mode and in a test mode and that the control/evaluation unit determines the ion concentration of the medium in the operating mode and reviews the proper functioning of the reference half cell in the test mode.

Preferably, an impedance, especially a resistance, is provided in the measuring circuit. An advantageous embodiment of the apparatus of the invention provides that, in the operating mode, the resistance is short circuited, while, in the test mode, the resistance is added into the measuring circuit. It is, of course, understood that any other kind of impedance change is usable in the measuring circuit in connection with the invention.

Preferably, an impedance changing element, e.g. a switch, is provided, which is connected in parallel with the resistance. This switch is actuated by the evaluation/control unit.

An advantageous embodiment of the apparatus of the invention provides that the control/evaluation unit interprets a change of the ratio of the noise portions in the operating mode and in the test mode, once the change lies above a predetermined threshold value, to the effect that the reference half cell is working correctly.

Especially, the control/evaluation unit outputs a malfunctioning of the reference half cell, when the relationship of the noise portion of the measurement signal in the operating mode and in the test mode is approximately unchanged.

For eliminating outliers from the measurement signals, the control/evaluation unit uses statistical evaluation methods for recognizing a malfunctioning and/or the correct operation of the reference half cell.

BRIEF DESCRIPTION OF THE DRAWINGS

The invention will now be explained in greater detail on the basis of the drawings, the figures of which show as follows.

DESCRIPTION OF THE PREFERRED EMBODIMENTS

Figure 1:
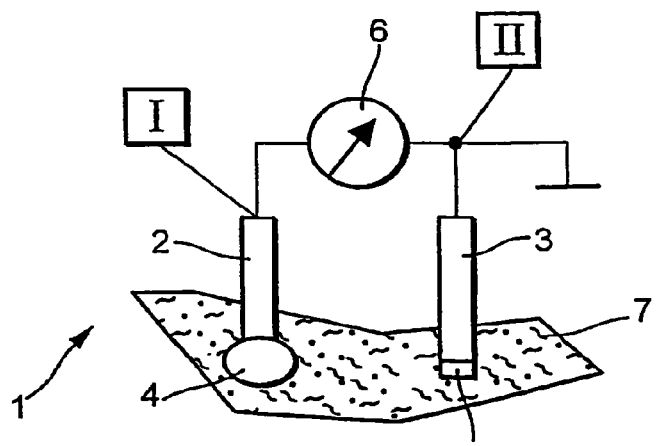
FIG. 1 a measuring point known from the state of the art for measuring and/or monitoring the ion concentration of a medium.
Figure 2:
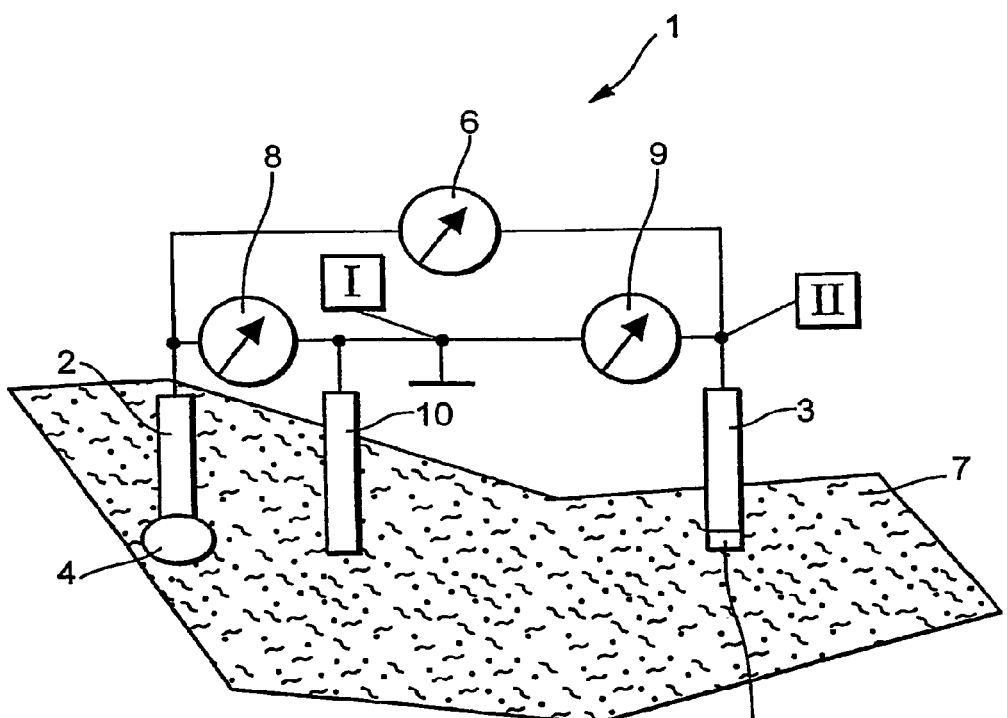
FIG. 2 a circuit known from the state of the art for monitoring the reference half cell of the measuring point shown in FIG. 1.

FIG. 1 shows a measuring point 1 known from the state of the art for measuring and/or monitoring the ion concentration of a medium 7. FIG. 2 shows a similarly known circuit known for monitoring the reference half cell 3 of the measuring point 1 for a blockage of the reference half cell 3. Both solutions have already been described sufficiently above in the introduction of this specification.

Figure 3:
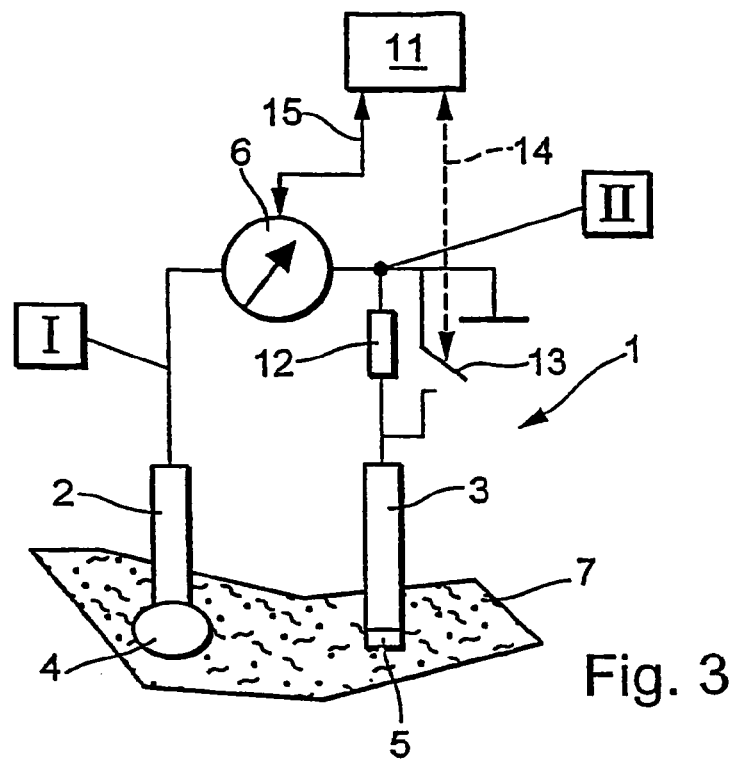
FIG. 3 a preferred embodiment of the apparatus of the invention for monitoring the reference half cell of a potentiometric measuring point.

FIG. 3 shows a preferred form of embodiment of the apparatus of the invention for monitoring the reference half cell 3 of a measuring point 1 serving for determining and/or monitoring the ion concentration of a medium 7. Especially, the measuring point 1 is a pH measuring point. The concept of the invention differs from the known concept shown in FIG. 1 in that, in the measuring circuit, a resistance 12 is provided, which has a switch 13 connected in parallel therewith. The switch is, as a rule, kept closed by the control/evaluation unit 11 in the operating, or measuring, mode and held open by unit 11 in the test mode. Therefore, in the operating mode, resistor 12 is short-circuited, i.e. the reference half cell 3 is connected at low resistance to the ground potential, while, in the test mode, a voltage drop occurs across the resistance 12.

A main component of the control/evaluation unit 11 is a microprocessor, which is not separately shown in FIG. 3. This serves together with a likewise not separately illustrated analog/digital converter for converting, calculating and presenting the measurement signal, or the measured value, as the case may be. Such control/evaluation units 11 are already available in the pH-transmitters of the assignee and thus are, per se, known in the state of the art.

The measurement signals, usually voltage values, which, for example, reflect the pH-value of the medium 7, are, however, in no way constant. Quite the contrary, an averaged, measured voltage value always has noise superimposed on it. If the switch 13 is open, then the reference half cell 3 is connected with the ground potential through the resistance 12 and the coupling to the ground potential becomes poorer. Therefore, the noise superimposed on the average value of the measurement signal also increases, as a function of the size of the resistance 12.

However, if the liquid-bridged reference half cell 3 is blocked and the impedance of the reference half cell 3 is in the vicinity of the added resistance 12, or greater than the added resistance 12, then the noise is changed only insignificantly by the added resistance 12.

According to the invention, the concept is utilized, that, on the basis of the noise portions of the measurement signals in the operating mode and in the test mode, statements can be made as regards blockage of the reference half cell 3. The measuring in the test mode lasts only a few milliseconds. During this time, the previously determined measured value must be held in the hold-state. In this way, it is prevented that a disturbed measured value is output for further processing.

Figure 4:
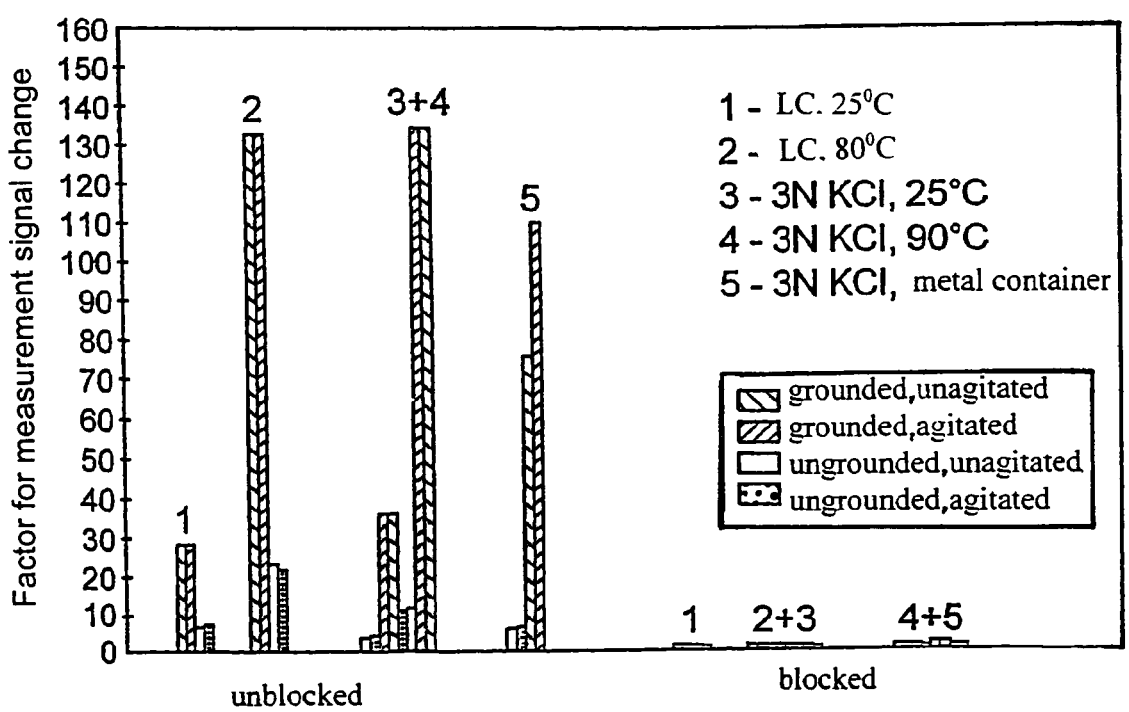
FIG. 4 a chart, in which the ratios of the noise portions of the measurement signals in the operating mode and in the test mode are presented for different conditions.

FIG. 4 is a bar chart showing the ratios of the noise portions of the measurement signals in the operating mode and in the test mode under different installation and operating conditions. Each of the four differently hatched bars represent four different working conditions, under which a potentiometric measuring point must deliver reliable measurement results at its installed location in industrial applications. In the case of ungrounded media being measured, external electromagnetic interference fields can negatively influence the measurements. In the case of turbulent, e.g. flowing media, local interference fields likewise occur.

In the case of the bars hatched from left-top to right-bottom, the medium 7 is at rest; additionally, the container, in which the medium is located, was grounded. In the case of the bars hatched from right-top to left-bottom, a turbulent, e.g. flowing, medium 7 is involved; also in this case, the container is grounded. In the case of the empty bars, the container is ungrounded and the medium at rest. In the case of the speckled bars, the container is ungrounded and the medium turbulent.

Numerals 1-5 indicate working conditions (in terms of different media at different temperatures), under which the measuring point is used. Numeral 1 is for a medium of low conductivity (LC) at a relatively low temperature, while numeral 2 is for a medium of low conductivity at a higher temperature. In the case of numerals 3 and 4, the measurements take place in an acid at different temperatures. Numeral 5 references the case in which the medium is an acid and the medium additionally is in a metal container.

In the left part of the bar chart, the percentage changes of the noise in the operating mode and in the test mode are presented for all the above-listed conditions of use, for the case that the reference half cell 3 is unblocked. Even in the least favorable case, the noise component in the operating mode is greater than the noise component in the test mode, by a factor of 5. In the right part of the bar chart, the percentage changes of the noise in the operating mode and in the test mode are shown for a blocked reference half cell 3. It is clearly evident that the noise in both modes is almost constant. According to the invention, an approximately unchanged noise component in the operating mode and in the test mode is a clear indication of a malfunctioning of the reference half cell.

The invention claimed is:

1. In a measuring point including a reference half cell and a measuring half cell, a method for monitoring the reference half cell for determining or monitoring an ion concentration of a medium, the ion concentration of the medium being determined on the basis of at least one measurement signal determined between the measuring half cell and the reference half cell, the method comprising the steps of:
   intermittently operating the measuring point in an operating mode and in a test mode;
   measuring the ion concentration in the operating mode;
   checking the proper functioning of the reference half cell in the test mode;
   measuring the noise components of the measurement signals in the operating mode and in the test mode;
   recognizing a malfunctioning of the reference half cell on the basis of a relationship of the changes of the noise components in the operating mode and in the test mode; and
   outputting a corresponding report.

2. The method as claimed in claim 1, further comprising the step of:
   determining the noise component of the measurement signal in the test mode and in the operating mode.

3. The method as claimed in claim 2, further comprising the steps of:
   activating an impedance in the test mode in a measuring circuit for determining the noise component; and
   changing the impedance in the operating mode.

4. The method as claimed in claim 3, wherein:
   an impedance-changing element is activated for the purpose of changing the impedance.

5. The method as claimed in claim 4, wherein:
   a switch is actuated as the impedance-changing-element, which is connected in parallel with the impedance for the purpose of changing the impedance.

6. The method as claimed in claim 1, further comprising the steps of:
   continually storing the noise components of the measurement signals, or the relationships of the changes of the noise components of the measurement signals in the operating mode and in the test mode; and
   outputting a report, concerning after which length of time the reference half cell will probably exhibit a malfunction.

7. In a measuring point including a reference half cell and a measuring half cell, an apparatus for determining or monitoring an ion concentration of a medium, the apparatus comprising:
   said measuring point;
   a measuring circuit located between the measuring half cell and the reference half cell; and
   a control and evaluation unit, which determines the ion concentration of the medium on the basis of a measurement signal determined in said measuring circuit, wherein:
   said control and evaluation unit operates the measuring point intermittently in an operating mode and in a test mode; and
   said control and evaluation unit determines the ion concentration of the medium in the operating mode and checks the proper functioning of the reference half cell in the test mode, wherein;
   said control and evaluation unit interprets a change of the relationship of the noise components in the operating mode and in the test mode as an indication that the reference half cell is working correctly, as soon as the change lies above a predetermined threshold value.

8. The apparatus as claimed in claim 7, wherein:
in said measuring circuit, an impedance is provided, which is changed, preferably short-circuited, in the operating mode and is added into said measuring circuit in the test mode.

9. The apparatus as claimed in claim 8, further comprising:
an impedance changing element, which is connected in parallel with the impedance; and
said impedance changing element is actuated by said control and evaluation unit.

10. The apparatus as claimed in claim 7, wherein:
said control and evaluation unit outputs a malfunctioning of the reference half cell, when the relationship of the noise components of the measurement signal in the operating mode and in the test mode is approximately unchanged.

11. Apparatus as claimed in claim 7, wherein:
said control and evaluation unit uses statistical evaluation methods for recognizing a malfunctioning, or the correct working, of the reference cell.

* * * * *